United States Patent [19]
Hirashima et al.

[11] Patent Number: 5,397,804
[45] Date of Patent: Mar. 14, 1995

[54] INDUSTRIAL MICROBICIDE AND A METHOD FOR KILLING MICROBES FOR INDUSTRIAL USE

[75] Inventors: Hidenori Hirashima, Osaka; Yoshimasa Yamada, Suita, both of Japan

[73] Assignee: Katayama Chemical Incorporated, Osaka, Japan

[21] Appl. No.: 34,556

[22] Filed: Mar. 19, 1993

[51] Int. Cl.$^6$ .............................................. A01N 33/24
[52] U.S. Cl. ................................................... 514/640
[58] Field of Search ......................................... 514/640

[56] References Cited

U.S. PATENT DOCUMENTS

| | | | |
|---|---|---|---|
| 3,790,687 | 2/1974 | Bertin et al. | 424/327 |
| 3,968,240 | 7/1976 | Takahashi et al. | 424/311 |

FOREIGN PATENT DOCUMENTS

| | | | |
|---|---|---|---|
| 50-15844 | 6/1975 | Japan | A01N 9/20 |
| 51-33171 | 4/1976 | Japan | A01N 9/20 |
| 54-36647 | 11/1979 | Japan | A01N 9/20 |
| 1-151502 | 6/1989 | Japan | A01N 43/26 |
| 3-83902 | 4/1991 | Japan | A01N 43/10 |
| 3-167101 | 7/1991 | Japan | A01N 37/00 |
| 3-170404 | 7/1991 | Japan | A01N 37/00 |

OTHER PUBLICATIONS

Perold et al, C.A. vol. 51 (1957) 6603f.

*Primary Examiner*—Allen J. Robinson
*Attorney, Agent, or Firm*—Cohen, Pontani, Lieberman, Pavane

[57] ABSTRACT

An industrial microbicide comprising α-chlorobenzaldoxime and optionally known industrial microbicidal which is useful for antiseptis or microbicidal of papermaking water in a paper/pulp industry.

7 Claims, 1 Drawing Sheet

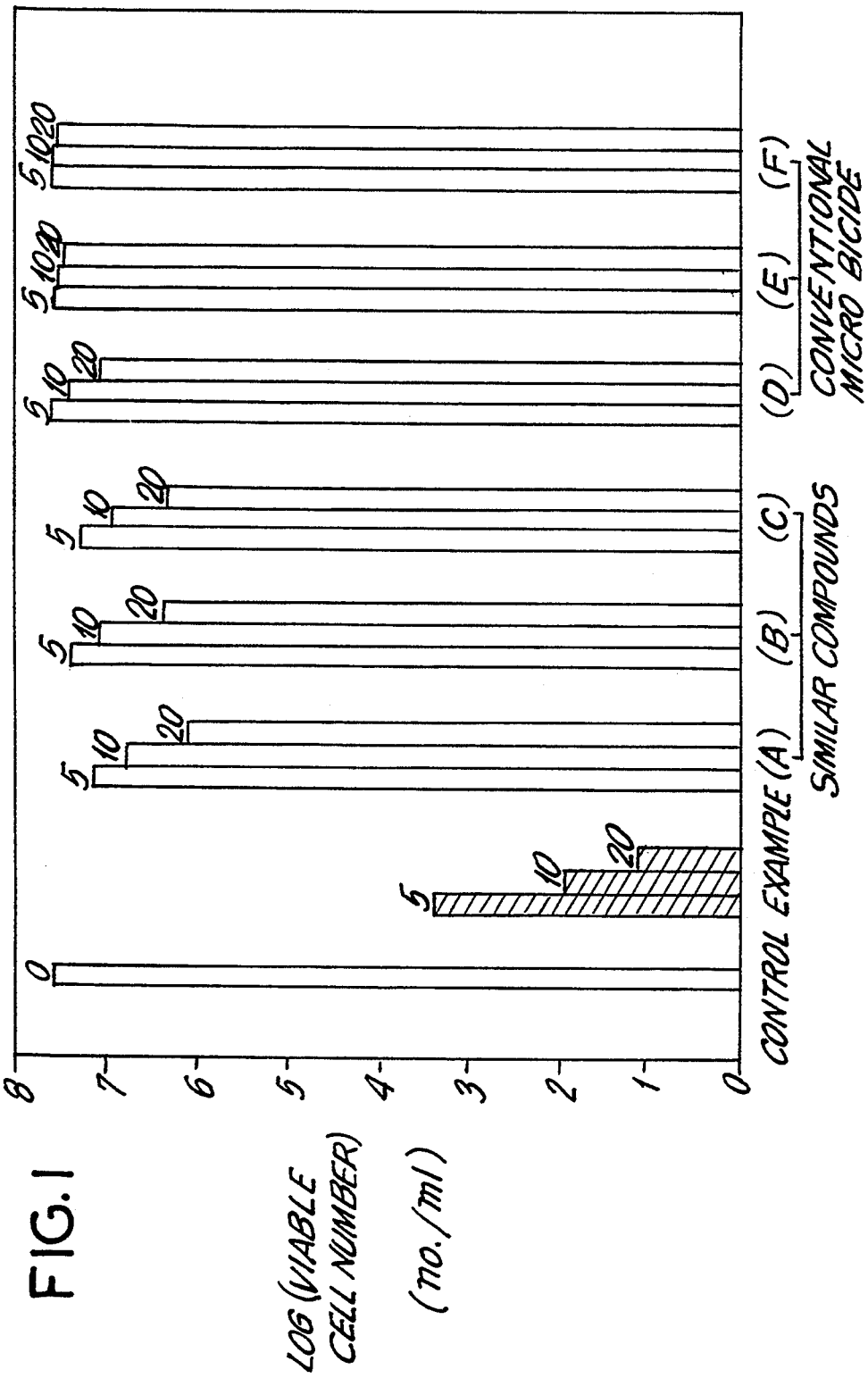

INDUSTRIAL MICROBICIDE AND A METHOD FOR KILLING MICROBES FOR INDUSTRIAL USE

BACKGROUND OF THE INVENTION

1. Field of the Invention

The invention relates to an industrial microbicide and a method of killing microbes for industrial use, and more particularly to an industrial microbicide and a method of killing microbes for industrial use to antisepsis or microbicidal of papermaking water in a paper/pulp industry, cooling water and washing water in various industries, heavy oil sludges, cutting fluids, textile oils, paints, paper coating liquids, latices and sizings. 2. Description of the Prior Art Slimes generated due to the growth of bacteria and/or fungi in cooling water and process water of the paper/pulp industry or various industries deteriorate a quality of products and efficiency of production. Further, in various industrial products, such as heavy oil sludges, cutting fluids, textile oils, paints, various latices and sizings, putrefaction and contamination occur due to the growth of bacteria and/or fungi which reduces their value.

For the prevention of these problems produced by such microorganism, many microbicides have been used. Previously, organomercury compounds and chlorinated phenols were used for this purpose. However, the use of these compounds is to be regulated, because they have a strong toxicity to the human body, fish and shellfish and may cause environmental pollution.

Lately, organonitrogen-sulfur compounds, organohalide compounds and organosulfur compounds which have relatively low toxicity, are practically used [see BOKIN-BOKABI-JITEN (Dictionary of Antibacterial and Antifungal Agent) published by Antibacterial and Antifungal Society, 1986; Japanese Laid-Open Patent Publication Nos. (HEI) 3-170404/1991, 3-83902/1991 and 3-167101/1991].

As examples of these types of microbicides, α-chloro-O-acylbenzaldoximes derived from α-chlorobenzaldoxime and α-chloro-chlorobenzaldoximes are known (see Japanese Patent Publication Nos. (SHO) 50-158844/1975, 54-36647/1979 and 51-33171/1976).

However, it is not known that α-chlorobenzaldoxime itself shows a potent microbicidal property in industrial media.

The conventional organic microbicides and the above microbicides exhibit effective microbicidal effect when used in non-reductive industrial media. However, when the conventional organic microbicides are used in the presence of a reducing agent such as sulfite ion, the microbicidal activity is significantly reduced, whereby the problems mentioned above can not be solved.

SUMMARY OF THE INVENTION

The present invention provides an industrial microbicide comprising α-chlorobenzaldoxime as an active ingredient.

The present invention also provides a method of killing microbes for in an industrial medium use by adding α-chlorobenzaldoxime and known industrial microbicidal ingredients simultaneously or separately.

BRIEF DESCRIPTION OF THE DRAWINGS

FIG. 1 is a diagram showing the microbicidal effect according to the test example 2.

PREFERRED EMBODIMENTS OF THE INVENTION

The present invention provides an industrial microbicide comprising α-chlorobenzaldoxime as an active ingredient.

The present invention is based on the fact that α-chlorobenzaldoxime itself, which is an intermediate of conventional benzaldoxime derivative microbicides, exhibits a remarkable and significant microbicidal effect under reductive conditions and can be used as a microbicide more effectively than the conventional benzaldoximes.

α-Chlorobenzaldoxime has a formula (I) as follows:

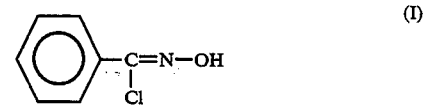

(I)

The microbicide of the present invention is preferably formulated in the form of a liquid preparation. As a diluent or carrier for the formulation, general organic solvents are useful. In particular, hydrophilic organic solvents are preferable when the microbicide is used for various water systems such as papermaking process water, paper coating liquid and sizing in paper/pulp industry. Examples of the hydrophilic organic solvents include diethylene glycol, polyethylene glycol, propylene carbonate and dimethyl glutarate. The above mentioned ingredient can be used in neat or in the combination with a conventional suitable solid carrier or diluent.

The microbicide of the present invention exhibits a significant microbicidal effect when used in a medium of various industrial systems, and is especially useful as a microbicide for the above mentioned papermaking water, paper coating liquid, sizing and so on. Particularly, an excellent microbicidal effect can be exhibited in an industrial medium containing a reducing agent equal to or greater than 5 mg/l in terms of sulfite ions, for example, papermaking process water containing deinked pulp (DIP).

The suitable amount of the active ingredient to be added to an industrial medium depends on the conditions of the medium. Generally, the compound having the formula (I) is preferably used in the amount of about 0.5 to 50 mg/l.

Further, some additives (for example, surface active agents and soluble polymers for improving the stability in dispersion liquid) can be added if the effect of the present invention is not reduced. Other known industrial microbicidal ingredients can be also included.

And the present invention provides also an industrial microbicide comprising α-chlorobenzaldoxime and a known industrial microbicidal ingredient. The combined use is effective in expanding the antibacterial spectrum and developing the additive or synergistic effect of antibacterial activity.

The known industrial microbicidal ingredients include organonitrogen-sulfur compounds, organobromine compounds, organonitrogen compounds, organosulfur compounds and other known industrial ingredients.

Examples of the organonitrogen-sulfur compounds include methylenebis(thiocyanate); 3-isothiazolone compounds such as 5-chloro-2-methyl-4-isothiazolin-3-one, 2-methyl-4-isothiazolin-3-one, 4,5-dichloro-2-n- octyl-isothiazolin-3-one, 2-n-octyl-isothiazolin-3-one and 1,2-benzisothiazolin-3-one; dithiocarbamates such as ammonium N-methyldithiocarbamate, sodium N-methyldithiocarbamate, sodium dimethyldithiocarbamate, ethylenethiuram monosulfide, disodium ethylenebis(dithiocarbamate) and manganese ethylenebisdithiocarbamate; sulfonamides such as chloramine T and N,N-dimethyl-N'-(fluorodichloromethylthio)-N'-phenylsulfamide; thiazole compounds such as 2-(4-thiocyanomethylthio)benzothiazole and sodium benzothiazole-2-thiolate; S-triazine compounds such as hexahydro-1,3,5-tris-(2-ethyl)-S-triazine or hexahydro-1,3,5-tris-(2-hydroxyethyl)-5-triazine; N-(fluorodichloromethylthio)-phthalimide; 3,5-dimethyl-1,3,5-2H-tetrahydrothiazine-2-thione; and dithio-2,2'-bis(benzylamide).

Examples of the organobromine compounds include organobromo cyano compounds such as 2,2-dibromo-3-nitrilopropionamide and 2-bromo-2-bromomethyl-glutaronitrile; organobromino-nitro compounds such as 2-bromo-2-nitropropane-1,3-diol, 1,1-dibromo-1-nitro-2-propanol, 2,2-dibromo-2-nitro-1-ethanol, 1,1-dibromo-1-nitro-2-acetoxyethane, 1,1-dibromo-1-nitro-2-acetoxypropane, 2-bromo-2-nitro-1,3-diacetoxypropane, tribromonitroethane, β-bromo-β-nitrostylene, 5-bromo-5-nitro-1,3-dioxane and 5-bromo-5-methyl-5-nitro-1,3-dioxane; bromoacetic esters or amides thereof such as 1,2-bis(bromoacetoxy)ethane, 1,2-bis(bromoacetoxy)propane, 1,4-bis(bromoacetoxy)-2-butene, methylene bis(bromoacetate), benzyl bromoacetate, N-bromoacetamide and 2-bromoacetamide; 2-bromo-4'-hydroxyacetophenone; 2,5-dichloro-4-bromophenol; 2,4,6-tribromophenol; α-bromocinnamaldehyde; bistribromomethylsulfone; 2-hydroxyethyl 2,3-dibromopropionate.

Examples of the organonitrogen compounds include N-(4-dihydroxy)-α-oxobenzeneethanimidoyl chloride; chlorinated isocyanuric acid compounds such as sodium dichloroisocyanurate and trichloroisocyanuric acid; quaternary ammonium compounds such as dequalinium chloride, laurylisoquinolium bromide and benzalconium chloride; carbamic acids or esters thereof such as methyl 2-benzimidazole carbamate and 3-iodo-2-propargylbultylcarbamate; imidazoles such as 1-[2-(2,4-dichlorophenyl)]-2'-[(2,4-dichlorophenyl)methoxy]ethyl-3-(2-phenylethyl)-1H-imidazolium chloride and 1-[2-(2,4-dichlorophenyl)-2-(2-propenyloxy)ethyl]-1H-imidazole; amides such as 2-(2-furyl)-3-(5-nitro-2-furyl)-acrylamide and 2-chloroacetamide; aminoalcohols such as N-(2-hydroxypropyl)-aminomethanol and 2-(hydroxymethylamino) ethanol; mono- or dihalogenated glyoximes such as monochloroglyoxime, monobromoglyoxime, monofluoroglyoxime, monoiodoglyoxime, dichloroglyoxime, dibromoglyoxime, difluoroglyoxime and diiodoglyoxime; sodium salt of 2-pyridinethiol 1-oxide; 2,4,5,6-tetrachloroisophthalonitrile; N-(2-methyl-1-naphthyl)maleimide and polyoxyethylene(dimethylimino) ethylene(dimethylimino)ethylene-dichloride].

Examples of the organosulfur compounds include 4,5-dichloro-1,2-dithiol-3-one; 3,3,4,4-tetrachlorotetrahydrothiophene-1,1-dioxide; dithio-2,2'-bis(1-benzmethylamide); 2-hydroxypropyl methanethiosulfonate; and ethylenethiuram monosulfide.

The other known microbicidal ingredients include 3-acetoxy-1,1,2-triiodo-1-propene; glutaric dialdehyde; dichlorophene; hydrogen peroxide; and maleic anhydride.

From the view point of synergistic effect exhibited by the combined use with α-chlorobenzaldoxime, preferable compounds chosen from among the known industrial microbicidal ingredients are described below.

As for the organonitrogen-sulfur compounds, methylenebis(thiocyanate); and 3-isothiazoline compounds such as 5-chloro-2-methyl-4-isothiazolin-3-one, 2-methyl4-isothiazolin-3-one, 4,5-dichloro-2-n-octylisothiazolin-3-one, 2-n-octylisothiazolin-3-one, and 1,2-benzoisothiazolin-3-one are preferable. More preferably, methylenebis(thiocyanate), 5-chloro-2-methyl-4-isothiazolin-3-one and 4,5-dichloro-2n-octyl-isothiazolin-3-one exhibit significant synergistic effect.

As for the organobromine compounds, following compounds are preferable: organobromic cyano compounds such as 2,2-dibromo-3-nitrilopropionamide and 2-bromo-2-bromomethylglutaronitrile; organobrominenitro compounds such as 2-bromo-2-nitropropane-1,3-diol, 2,2-dibromo-2-nitro-1-ethanol, 1,1-dibromo-1-nitro-2-propanol, 2,2-dibromo-2-nitro-1-ethanol, 1,1-dibromo-1-nitro-2-acetoxyethane, 1,1-dibromo-1-nitro-2-acetoxypropane, 2-bromo-2-nitro-1,3-diacetoxy-propane, tribromonitromethane, β-bromo-β-nitrostylene, 5-bromo-5-nitro-1,3-dioxane and 5-bromo-2-methyl-5-nitro-1,3dioxane; organobromoacetic esters or amides thereof such as 1,2-bis(bromoacetoxy)ethane, 1,2-bis(bromoacetoxy)propane, 1,4-bis(bromoacetoxy)-2-butene, methylene bis(bromoacetate), benzyl bromoacetate, N-bromoacetamide and 2-bromoacetamide. More preferably, 2,2-dibromo-3-nitrilopropionamide, 2-bromo-2-bromomethyl-glutaronitrile 2,2-dibromo-2-nitro-1-ethanol, 2-bromo-2-nitro-1,3-diacetoxypropane, 1,2-bis(bromoacetoxy)ethane, 1,2bis-(bromoacetoxy)-propane, 1,4-bis(bromoacetoxy)-2-butene and N-bromoacetamide exhibit significant synergistic effect.

As for the organonitrogen compounds, N-(4-dihydroxy)-α-oxobenzeneethanimidoyl chloride, monochloroglyoxime and dichloroglyoxime exhibit significant synergistic effect.

As for the organosulfur compounds, 4,5-dichloro-1,2-dithiol-3-one and 3,3,4,4-tetrachlorotetrahydrothiophene-1,1-dioxide exhibit significant synergistic effect.

The mixing ratio of α-chlorobenzaldoxime and the known industrial microbicidal ingredients in the present invention to obtain a significant synergistic effect is suitably 50:1 to 1:20 (by weight), more preferably, 20:1 to 1:10.

Also, two or more known industrial microbicidal ingredients can be used in combination.

When α-chlorobenzaldoxime and known industrial microbicidal ingredients are combined, it is preferable to formulate in the form of a single-pack liquid preparation.

In order to prepare the single-pack liquid preparation, organic solvents and dispersing agents are generally used. When the formulation is to be used in an industrial water system, such as in papermaking process water and industrial cooling water, the preparation preferably may be prepared by use of water or hydrophilic organic solvents and/or dispersing agents to ensure the solubility and dispersibility of the active ingredients in water. For industrial microbicidal dal products contained α-chlorobenzaldoxime having good storage stability for long time, liquid preparation preferably is formulated with hydrophilic organic solvents and/or nonionic surfactants. Examples of such hydrophilic organic solvents are amides such as dimethylformamide; glycols, such as ethylene glycol, propylene glycol, diethylene glycol and dipropylene glycol; glycolethers, such as methyl cellosolve, phenyl cellosolve, diethylene glycol monomethyl ether, dipropylene glycol monoethyl ether and tripropylene glycol monomethyl ether; alcohols having 1 to 8 carbon atoms; esters, such as methyl acetate, ethyl acetate, 3-methoxydibutyl acetate, 2-ethoxymethyl acetate, 2-ethoxyethyl acetate and propylenecarbonate.

The suitable dispersing agent includes cationic, anionic, nonionic and amphoteric surfactants. Preferable surfactant is nonionic surfactant because of its stability in formulations.

The nonionic surfactants include higher alcohol ethylene oxide adducts (hereinafter ethylene oxide is referred to E.O.), alkylphenol-E.O. adducts, fatty acid-E.O. adducts, fatty acid polyhydric alcohol ester-E.O. adducts, higher alkyl amine-E.O. adducts, fatty acid amide-E.O. adducts, fat and oil-E.O. adducts, propylene oxide (hereinafter referred to P.O.)-E.O. copolymers, alkylamine-P.O.-E.O. copolymer adducts, fatty acid glycerol esters, fatty acid pentaerythritol esters, fatty acid sorbitol esters, fatty acid sorbitan esters, fatty acid sucrose esters, polyhydric alcohol alkyl ethers and alkylolamides.

The preparation of the present invention preferably comprises 1 to 50 parts by weight of the total preparation of the active ingredients and at least 0.01 part by weight of the dispersing agent per part of the active ingredients, the balance being a hydrophilic organic solvent, from the view of stability for a long period of time.

For an oil medium such as heavy oil sludge, cutting oil or oily paint, a single-pack liquid preparation is formulated with a hydrocarbon solvent such as kerosene, heavy oil and spindle oil, and optionally containing the above-mentioned surfactant.

A suitable amount of the microbicide of the present invention to be added depends on the industrial medium to be added. In particular, to papermaking process water or industrial cooling water, the addition of about 0.05 to 20 mg/l as the total active ingredients concentration in the water will be sufficient for inhibiting the growth of microbes (bacteriostatic concentration) and the addition of 0.5 to 50 mg/l will achieve a microbicidal effect.

In case of simultaneously using α-chlorobenzaldoxime and known industrial microbicide ingredients, the above mentioned single-pack preparation is convenient for the method according to the present invention. However, if separate storage or separate addition is preferable upon circumstances, for example in case of keeping a stability for a long time, the separate preparations containing each of the active ingredients may be used.

Thus, the present invention provides a method of killing microbes for industrial use by adding α-chlorbenzaldoxime and optionally adding known industrial microbicidal ingredients to an industrial medium.

DESCRIPTION OF PREFERRED EMBODIMENTS

The present invention is described in detail with reference to examples and test examples.

Test Example 1: Microbicidal effect in the presence of reducing agents

By the use of Pseudomonous aeruginosa, which is a typical strain of gram negative bacteria identified in process water of paper/pulp industry, cooling water of various industries, paints, paper coating liquids, latices and sizings, microbicidal activity was examined in the presence of a reducing agent.

As a reducing agent, sodium sulfite was used. A bouillon broth was inoculated with the bacteria and preincubated. The obtained culture was added to sterilized water having $SO_3^{2-}$ at each concentration of 5, 10, 20, 50 mg/l so that the viable cell number becomes $106^6$ or more/ml. The active ingredients listed in table 1 were added to the resultant culture and shaken for 1 hour at 37° C. The number of surviving bacteria was measured to determine the minimum concentration (mg/l) of the active ingredients required to kill bacteria in the number of 99.9% or more in the initial viable number.

The results are shown in table 1.

As is obviously seen from table 1, the compound of the formula (I) exhibited more microbicidal effect in the presence of $SO_3^{2-}$ (5 to 50 mg/l) than the similar compounds and conventional compounds.

TABLE 1

MINIMUM CONCENTRATION OF ACTIVE INGREDIENT FOR KILLING MICROBES (mg/l)

| Microbicidal active ingredient | $SO_3^{2-}$ (mg/l) | | | | |
|---|---|---|---|---|---|
| | 0 | 5 | 10 | 20 | 50 |
| Example 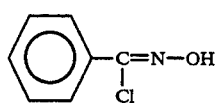 | 0.5 | 0.7 | 1 | 3 | 7 |
| Comparative Example (similar compounds) (A) 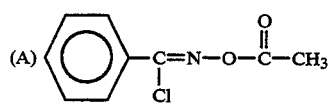 | 3 | 6 | 10 | 25 | 45 |

TABLE 1-continued

| Microbicidal active ingredient | MINIMUM CONCENTRATION OF ACTIVE INGREDIENT FOR KILLING MICROBES (mg/l) SO$_3^{2-}$ (mg/l) | | | | |
|---|---|---|---|---|---|
| | 0 | 5 | 10 | 20 | 50 |
| (B) 4-chloro-α-chlorobenzaldoxime 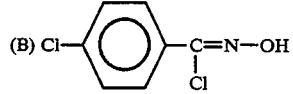 | 1 | 8 | 13 | 40 | 60 |
| (C) 2-chloro-α-chlorobenzaldoxime 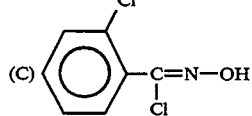 | 1 | 10 | 15 | 40 | 65 |

Comparative Examples
(conventional microbicide)

| | 0 | 5 | 10 | 20 | 50 |
|---|---|---|---|---|---|
| (D) 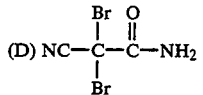 | 1 | 10 | 15 | 30 | 100 |
| (E) 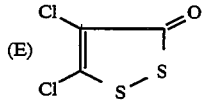 | 0.3 | 20 | 40 | 70 | 120 |
| (F) 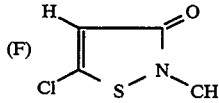 | 10 | 30 | 70 | 100 | 200 |

Test Example 2: Microbicidal effect in white water of paper-making process

In a certain paper mill, white water was sampled from a newsprint papermaking machine (for acid paper). The white water had a pH of 5.0, contained 30 mg/l of a reducing agent JISK0101 in terms of SO$_3^{2-}$ and mainly consisted of Pseudomonous, Flavobacterium and Bacillus species. The active ingredients listed in table 1 were added in the amount of 5, 10 and 20 mg/l to the white water and shaken for 1 hour at 37° C. and the number of surviving bacteria was measured.

The results are shown in FIG. 1.

As is obviously seen from FIG. 1, the compound of the formula (I) exhibited excellent microbicidal effect.

Formulation Example

Formulation examples in the present invention are as follows. These preparations are used in the form of liquid. The following numerical values show parts by weight.

(Formulation example 1)
| | |
|---|---|
| α-chlorobenzaldoxime | 15 |
| polyethylene glycol | 85 |

(Formulation example 2)
| | |
|---|---|
| α-chlorobenzaldoxime | 15 |
| diethylene glycol monomethyl ether | 85 |

(Formulation example 3)
| | |
|---|---|
| α-chlorobenzaldoxime | 15 |
| methylenebis(thiocyanate) | 10 |
| diethylene glycol monomethyl ether | 70 |
| dimethylformamide | 5 |

(Formulation example 4)
| | |
|---|---|
| α-chlorobenzaldoxime | 15 |
| 5-chloro-2-methyl-4-isothiazolin-3-one | 10 |
| diethylene glycol monomethyl ether | 70 |
| dimethylformamide | 5 |

(Formulation example 5)
| | |
|---|---|
| α-chlorobenzaldoxime | 15 |
| 4,5-dichloro-2-n-octyl-isothiazolin-3-one | 10 |
| diethylene glycol monomethyl ether | 70 |
| dimethylformamide | 5 |

(Formulation example 6)
| | |
|---|---|
| α-chlorobenzaldoxime | 15 |
| 2,2-dibromo-3-nitrilopropionamide | 10 |
| diethylene glycol monomethyl ether | 70 |
| dimethylformamide | 5 |

(Formulation example 7)
| | |
|---|---|
| α-chlorobenzaldoxime | 15 |
| 2-bromo-2-nitropropane-1,3-diol | 10 |
| diethylene glycol monomethyl ether | 70 |
| dimethylformamide | 5 |

(Formulation example 8)
| | |
|---|---|
| α-chlorobenzaldoxime | 15 |
| 2,2-dibromo-2-nitro-1-ethanol | 10 |
| diethylene glycol monomethyl ether | 70 |
| dimethylformamide | 5 |

(Formulation example 9)
| | |
|---|---|
| α-chlorobenzaldoxime | 15 |
| 2-bromo-2-nitro-1,3-diacetoxypropane | 15 |
| dimethyl succinate | 70 |

(Formulation example 10)
| | |
|---|---|
| α-chlorobenzaldoxime | 15 |
| 1,2-bis-(bromoacetoxy)-ethane | 15 |
| dimethyl succinate | 70 |

(Formulation example 11)
| | |
|---|---|
| α-chlorobenzaldoxime | 15 |
| 1,2-bis(bromoacetoxy)propane | 15 |
| dimethyl succinate | 70 |

(Formulation example 12)
| | |
|---|---|
| α-chlorobenzaldoxime | 15 |

-continued

| | |
|---|---|
| 1,4-bis(bromoacetoxy)-2-butene | 15 |
| dimethyl succinate | 70 |
| (Formulation example 13) | |
| α-chlorobenzaldoxime | 15 |
| 3,3,4,4-tetrachlorothiophene-1,1-dioxide | 10 |
| diethylene glycol monomethyl ether | 70 |
| dimethylformamide | 5 |
| (Formulation example 14) | |
| α-chlorobenzaldoxime | 15 |
| 2-bromo-2-bromomethyl-glutaronitrile | 10 |
| diethylene glycol monomethyl ether | 70 |
| dimethylformamide | 5 |
| (Formulation example 15) | |
| α-chlorobenzaldoxime | 15 |
| N-(4-dihydroxy)-α-ooxobenzeneethan imidoyl chloride | 10 |
| diethylene glycol monomethyl ether | 70 |
| dimethylformamide | 5 |
| (Formulation example 16) | |
| α-chlorobenzaldoxime | 15 |
| 4,5-dichloro-1,2-dithiol-3-one | 2 |
| diethylene glycol monomethyl ether | 83 |
| (Formulation example 17) | |
| α-chlorobenzaldoxime | 15 |
| 4,5-dichloro-1,2-dithiol-3-one | 10 |
| diethylene glycol monomethyl ether | 40 |
| polyethylene glycol 200 | 35 |
| (Formulation example 18) | |
| (α-chlorobenzaldoxime | 15 |
| 4,5-dichloro-1,2-dithiol-3-one | 4 |
| diethylene glycol monomethyl ether | 76 |
| dimethylformamide | 5 |
| (Formulation example 19) | |
| α-chlorobenzaldoxime | 10 |
| monochloroglyoxime | 10 |
| diethylene glycol monomethyl ether | 79 |
| nonylphenol EO (10 moles) adducts | 1 |
| (Formulation example 20) | |
| α-chlorobenzaldoxime | 10 |
| dichloroglyoxime | 10 |
| diethylene glycol monomethyl ether | 79 |
| nonylphenol EO (10 moles) adducts | 1 |
| (Formulation example 21) | |
| α-chlorobenzaldoxime | 10 |
| monochloroglyoxime | 5 |
| dichloroglyoxime | 5 |
| diethylene glycol monomethyl ether | 79 |
| nonylphenol EO (10 moles) adducts | 1 |
| (Formulation example 22) | |
| α-chlorobenzaldoxime | 10 |
| monochloroglyoxime | 9.5 |
| dichloroglyoxime | 0.5 |
| diethylene glycol monomethyl ether | 79 |
| nonylphenol EO (10 moles) adducts | 1 |
| (Comparative formulation example 1) | |
| 4,5-dichloro-1,2-dithiol-3-one | 20 |
| diethylene glycol monomethyl ether | 80 |
| (Comparative formulation example 2) | |
| α-chlorobenzaldoxime | 20 |
| diethylene glycol monomethyl ether | 80 |

Test example 3: Synergistic effect on microbes by the combination of α-chlorobenzaldoxime and known industrial microbicide In a certain paper mill, white water was sampled from a newsprint papermaking machine (for acid paper). The white water had a pH of 5.1, contained 27 mg/l of $SO_3^{2-}$ and mainly consisted of Bacillus, Micrococcus, Pseudomonas, Flavobacterium and Alcaligenes species. The ingredients (A+B) listed in table 2 were added to the white water in the amount of 5 mg/l as the total amount of active ingredients and shaken for 30 minutes at 37° C. The number of surviving bacteria was measured and killing rate was calculated (initial number of bacteria $7.5 \times 10^5$ no./ml).

The results are shown in Table 2. The data in the table show the killing rate of bacteria (%).

TABLE 2

| | Killing Rate (%) | | | | | |
|---|---|---|---|---|---|---|
| | Composition of active ingredients A:B | | | | | |
| Ingredient B | 0:100 | 10:90 | 50:50 | 90:10 | 95:5 | 100:0 (wt %) |
| (a) | 10 | 50 | 65 | 55 | 50 | 30 |
| (b) | 5 | 35 | 45 | 65 | 65 | 30 |
| (c) | 5 | 40 | 50 | 65 | 70 | 30 |
| (d) | 20 | 45 | 95 | 75 | 60 | 30 |
| (e) | 20 | 40 | 70 | 55 | 50 | 30 |
| (f) | 15 | 35 | 75 | 60 | 55 | 30 |
| (g) | 15 | 50 | 80 | 70 | 60 | 30 |
| (h) | 15 | 45 | 65 | 60 | 50 | 30 |
| (i) | 10 | 40 | 70 | 65 | 50 | 30 |
| (j) | 15 | 50 | 75 | 65 | 55 | 30 |
| (k) | 20 | 55 | 80 | 70 | 60 | 30 |
| (l) | 10 | 45 | 70 | 55 | 50 | 30 |
| (m) | 25 | 50 | 70 | 80 | 75 | 30 |
| (n) | 20 | 50 | 95 | 75 | 60 | 30 |

A: α-chlorobenzaldoxime
B: At least one compound selected from (a) to (n) below:
(a) methylenebis(thiocyanate)
(b) 5-chloro-2-methyl-4-isothiazolin-3-one
(c) 4,5-dichloro-2-n-octyl-isothiazolin-3-one
(d) 2,2-dibromo-3-nitrilopropionamide
(e) 2-bromo-2-nitropropane-1,3-diol
(f) 2,2-dibromo-2-nitro-1-ethanol
(g) 2-bromo-2-nitro-1,3-diacetoxypropane
(h) 1,2-bis(bromoacetoxy)ethane
(i) 1,2-bis(bromoacetoxy)propane
(j) 1,4-bis(bromoacetoxy)2-butene
(k) 3,3,4,4-tetrachlorotetrahydrothiophene-1,1-dioxide
(l) 2-bromo-2-bromomethyl-glutaronitrile
(m) N-(4-dihydroxy)-α-ooxobenzeneethanimidoyl chloride
(n) N-bromoacetamide Test example 4: Synergistic effect on microbes by the combination of α-chlorobenzaldoxime and 4,5-dichloro-1,2-dithiol-3-one In a certain paper mill, white water was sampled from a newsprint papermaking machine (for acid paper). The white water had a pH of 5.1, contained 27 mg/l of $SO_3^{2-}$ and mainly consisted of Bacillus, Micrococcus, Pseudomonas, Flavobacterium and Alcaligenes species. The active ingredients (A+B+C) listed below were added each to the white water in the amount of 5 mg/l as the total amount of active ingredients and shaken for 30 minutes at 37° C. The number of surviving bacteria was measured and killing rate of bacteria was calculated (initial number of bacteria $7.5 \times 10^5$ no./ml). The results are shown in Table 3.

TABLE 3

| | Composition of active ingredients (5 mg/l in total) | | | Killing rate |
|---|---|---|---|---|
| Number | A (%) | B (%) | C (%) | (%) |
| 1 | 100 | 0 | — | 30 |
| 2 | 98 | 2 | — | 40 |
| 3 | 95 | 5 | — | 55 |
| 4 | 90 | 10 | — | 70 |
| 5 | 70 | 30 | — | 80 |
| 6 | 50 | 50 | — | 65 |
| 7 | 20 | 80 | — | 50 |
| 8 | 10 | 90 | — | 45 |
| 9 | 0 | 100 | — | 25 |
| 10 | — | 0 | 100 | 10 |
| 11 | — | 10 | 90 | 15 |
| 12 | — | 50 | 50 | 25 |

TABLE 3-continued

| Number | Composition of active ingredients (5 mg/l in total) A (%) | B (%) | C (%) | Killing rate (%) |
|---|---|---|---|---|
| 13 | — | 90 | 10 | 25 |

A: α-chlorobenzaldoxime
B: 4,5-dichloro-1,2-dithiol-3-one
C: α-chlorobenzaldoxime acetate
Note:
In the table above, numbers 1 to 8 represent examples of the present invention and numbers 9 to 13 are comparative examples, which 11 to 13 are disclosed in the Japanese Laid-Open Publication (HEI) 1-151502/1989.

Test example 5: Synergistic effect

At a certain newsprint papermaking machine (pH 4.5, $SO_3^{2-}$ 70 mg/l, and mainly consisting of Bacillus, Micrococcus, Pseudomonas, Flavobacterium and Alcaligenes species), the preparation products listed in Formulation Example were added to at head box for 30 minutes and the number of surviving bacteria was measured.

The results are shown in table 4.

TABLE 4

| Used preparation | Amount | Surviving microbes (no./ml) |
|---|---|---|
| BLANK | | $7.5 \times 10^6$ |
| Formulation Ex. 18 | 50 mg/l | $3.2 \times 10^4$ |
| Comparative | 50 mg/l | $7.1 \times 10^6$ |
| Formulation Ex. 1 | 100 mg/l | $4.5 \times 10^6$ |
| Comparative | 50 mg/l | $7.8 \times 10^5$ |
| Formulation Ex. 2 | 100 mg/l | $5.3 \times 10^4$ |

Test example 6: Microbistatic effect (1)

In a certain paper mill, white water having a pH of 7.5, containing 15 mg/l of $SO_3^{2-}$ and mainly consisting of Bacillus, Micrococcus, Pseudomonas and Flavobacterium species was sampled from a papermaking machine (for neutralized paper). The white water was filtered with No. 2 filter paper to prepare testing water. Bouillon broth was added to the testing water, then the resultant water was added to a previouly sterilized L shaped test tube. Next, active ingredients listed in table 6 were added to each concentration and shaken at 30° C. for 24 hours.

The minimum inhibitory concentration (MIC, 24h) of the ingredients was determined at which no growth of microbes was measured.

The results are shown in table 6.

TABLE 6

| | Composition of active ingredients (wt %) | | | | |
|---|---|---|---|---|---|
| | A 100% | (O) 100% | (P) 100% | A:(O) 1:1 | A:(O):(P) 2:1:1 |
| MIC 24 Hr | 4.5 | 3.0 | 4.0 | 0.7 | 0.5 |

TABLE 6-continued

| | Composition of active ingredients (wt %) | | | | |
|---|---|---|---|---|---|
| | A 100% | (O) 100% | (P) 100% | A:(O) 1:1 | A:(O):(P) 2:1:1 |
| (mg/l) | | | | | |

A: α-chlorobenzaldoxime
(O): monochloroglyoxime
(P): dichloroglyoxime

Test example 7: Microbistatic effect (2)

The testing water used in text example 6 was used.
Bouillon broth was added to the testing water, then the resultant was added to the previouly sterilized L shaped test tube.

Next, active ingredients were added each in the amount of 2.0 mg/l as the total active ingredient and shaken at 30° C. to incubate. The absorption at 660 nm was measured for 24 hours. The time (t) to be 0.1 in absorption was measured. The time T showing the inhibition of the growth of microbes is caluculated by the formula as follows:

$$T = t_x - t_0$$

wherein $t_0$ is a time (t) when no ingredient is added and $t_x$ is a time (t) when x mg of ingredients are added.

The results are shown in table 7.

TABLE 7

| Ingredients (2 mg/l) | Time T for inhibiting the growth of microbes (hour) Composition of active ingredients (wt %) | | | | | | | | |
|---|---|---|---|---|---|---|---|---|---|
| | 1:0 | 20:1 | 10:1 | 5:1 | 3:1 | 1:3 | 1:5 | 1:10 | 0:1 |
| A:(O) | 0 | 1 | 9 | >24 | >24 | >24 | >24 | 6 | 3 |
| A:(P) | 0 | 1 | 9 | >24 | >24 | >24 | >24 | 5 | 2 |

A: α-chlorobenzaldoxime
(O): monochloroglyoxime
(P): dichloroglyoxime

According to the industrial microbicide in the present invention, effective treatment can be conducted in various industrial microbicidal media. Paticularly, significantly high microbicidal effect under reductive conditions can be realized compared with conventional industrial microbicides.

What we claim is:

1. An industrial microbicidal composition comprising α-chlorobenzaldoxime in an amount of from 1 to 50 parts by weight as an active ingredient and a hydrophilic organic solvent as the remainder.

2. The microbicidal composition according to claim 1, wherein the hydrophilic organic solvent is diethylene glycol monomethyl ether.

3. A method of killing microbes in an industrial medium comprising adding a microbicidally effective amount of α-chlorobenzaldoxime to the industrial medium.

4. The method according to claim 3, wherein the microbicidally effective amount ranges from about 0.5 to 50 mg/l.

5. The method according to claim 3, wherein the industrial medium comprises a reducing agent.

6. The method according to claim 5, wherein the reducing agent is present in an amount of at least 5 mg/l.

7. The method according to claim 5, wherein the reducing agent comprises sulfite ions.

* * * * *